United States Patent
Tanioka

(10) Patent No.: US 9,550,042 B2
(45) Date of Patent: Jan. 24, 2017

(54) CATHETER

(75) Inventor: Hiromichi Tanioka, Fujinomiya (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 665 days.

(21) Appl. No.: 13/368,124

(22) Filed: Feb. 7, 2012

(65) Prior Publication Data

US 2012/0136340 A1 May 31, 2012

Related U.S. Application Data

(63) Continuation of application No. PCT/JP2010/065020, filed on Sep. 2, 2010.

(30) Foreign Application Priority Data

Sep. 15, 2009 (JP) .................. 2009-213583

(51) Int. Cl.
*A61M 25/00* (2006.01)
*A61M 25/01* (2006.01)

(52) U.S. Cl.
CPC ..... *A61M 25/0169* (2013.01); *A61M 25/0052* (2013.01); *A61M 2025/0183* (2013.01)

(58) Field of Classification Search
CPC .............. A61M 25/0052; A61M 25/00; A61M 25/0012; A61M 25/005; A61M 25/0053; A61M 25/0054; A61M 25/0029; A61M 25/0045; A61M 25/00183; A61M 25/0177; A61M 2025/0183; A61M 2025/0177; A61M 25/0169

(Continued)

(56) References Cited

U.S. PATENT DOCUMENTS 5,395,349 A * 3/1995 Quiachon .......... A61B 17/3462
                                                   251/4
5,413,560 A * 5/1995 Solar ..................... A61F 2/95
                                                   604/164.01

(Continued)

FOREIGN PATENT DOCUMENTS

EP        0 925 801 A1     6/1999
JP       2000-000309 A     1/2000

(Continued)

OTHER PUBLICATIONS

International Search Report (PCT/ISA/210) issued on Nov. 2, 2010, by Japanese Patent Office as the International Searching Authority for International Application No. PCT/JP2010/065020.

(Continued)

*Primary Examiner* — Quynh-Nhu H Vu
(74) *Attorney, Agent, or Firm* — Buchanan Ingersoll & Rooney PC

(57) ABSTRACT

A catheter which exhibits excellent anti-kinking properties while avoiding interference with respect to an object moving inside the lumen of the catheter includes: an elongated catheter main body having a longitudinally extending lumen; a tubular-shaped guide wire insertion portion on the distal end of the catheter main body through which a guide wire is insertable, and which includes a distal opening portion and a proximal opening portion; and a reinforcement portion having a coil portion in which at least a portion of the reinforcement portion is arranged proximally of the proximal opening portion and is formed by a wound wire element, and an extension portion extending from the wire element of the coil portion in the distal direction away from the proximal opening portion, and wherein the reinforcement portion is positioned between the inner surface and the outer surface of the lumen of the catheter main body.

26 Claims, 10 Drawing Sheets

(58) Field of Classification Search
USPC ......... 604/523, 524, 526, 527, 525; 600/109
See application file for complete search history.

(56) References Cited

U.S. PATENT DOCUMENTS

| | | | |
|---|---|---|---|
| 6,485,457 | B1 | 11/2002 | Hisamatsu et al. |
| 8,002,763 | B2* | 8/2011 | Berthiaume .............. A61F 2/95 600/585 |
| 2002/0038103 | A1* | 3/2002 | Estrada ................ A61M 25/09 604/103.09 |
| 2002/0161273 | A1* | 10/2002 | Farnan ............. A61M 25/0068 600/3 |
| 2002/0177841 | A1* | 11/2002 | Moloney ........... A61M 25/0052 604/528 |
| 2003/0208221 | A1* | 11/2003 | El-Nounou ......... A61M 25/104 606/191 |
| 2004/0087932 | A1* | 5/2004 | Lawrence ........... A61M 25/005 604/524 |
| 2004/0106866 | A1* | 6/2004 | Ookubo et al. ............... 600/437 |
| 2004/0116915 | A1* | 6/2004 | Lentz .............................. 606/21 |
| 2004/0236215 | A1* | 11/2004 | Mihara ............. A61M 25/0068 600/434 |
| 2005/0197669 | A1 | 9/2005 | Fisher |
| 2005/0267442 | A1* | 12/2005 | Von Oepen ................... 604/509 |
| 2006/0074402 | A1* | 4/2006 | Lawrece et al. .............. 604/526 |
| 2007/0167065 | A1* | 7/2007 | Melsheimer et al. ........ 439/404 |
| 2007/0203474 | A1* | 8/2007 | Ryan et al. ................... 604/528 |
| 2009/0018393 | A1* | 1/2009 | Dick et al. .................... 600/109 |
| 2009/0270838 | A1* | 10/2009 | Berthiaume .............. A61F 2/95 604/524 |
| 2010/0324537 | A1* | 12/2010 | Berthiaume .............. A61F 2/95 604/523 |

FOREIGN PATENT DOCUMENTS

| | | | | |
|---|---|---|---|---|
| JP | 2000-042115 | * | 2/2000 | ........... A61M 25/00 |
| JP | 2000-042115 | A | 2/2000 | |
| JP | 2001-095923 | A | 4/2001 | |
| JP | 2004-130110 | A | 4/2004 | |
| WO | 01/70323 | A1 | 9/2001 | |
| WO | 2005/007227 | A1 | 1/2005 | |

OTHER PUBLICATIONS

Extended Search Report issued by the European Patent Office on Mar. 6, 2013, in the corresponding European Application No. 10817051.5. (7 pages).

* cited by examiner

CATHETER

This application is a continuation of International Application No. PCT/JP2010/065020 filed on Sep. 2, 2010, and claims priority to Japanese Application No. 2009-213583 filed on Sep. 15, 2009, the entire content of both of which is incorporated herein by reference.

TECHNICAL FIELD

The present invention generally relates to a catheter. More specifically, the invention involves a catheter having useful application for being inserted inside a body lumen such as a blood vessel, a vascular channel and the like.

BACKGROUND DISCUSSION

Catheters to be inserted inside a body lumen such as a blood vessel, a vascular channel and the like are typically so-called "rapid-exchange type" catheters in which it is possible to relatively rapidly carry out the pulling-in and the pulling-out of a guide wire because there is provided, on the distal side of the catheter main body including a working lumen, a guide wire insertion portion having a tubular shape into which the guide wire is insertable. European Application Publication No. 0 925 801 describes an example of a rapid-exchange type balloon catheter. This balloon catheter is provided with a coil in the inside on the distal side of an inflation lumen (working lumen), and an anti-kink property in the vicinity of an opening portion of a guide wire insertion portion is improved by providing an extension portion which extends from the coil to the distal side away from the opening portion on the proximal side of the guide wire insertion portion.

However, the catheter described in European Application Publication No. 0 925 801 is configured such that the coil is exposed inside the working lumen. If this coil is used with a catheter in which a sensor is passed through the working lumen such as a catheter for diagnosis or the like which utilizes ultra-sound image diagnosis technology or optical coherence tomographic image diagnosis technology, there exists a possibility that when the catheter is bent, a portion of the sensor or the like interferes with the coil and is bit into between element wires or windings constituting the coil.

SUMMARY

According to one aspect, a catheter comprises: an elongated catheter main body having an axially extending lumen; a guide wire insertion portion at the distal end portion of the catheter main body, with a through hole passing through the guide wire insertion portion and configured to receive a guide wire allowing the catheter to be guided to a target site in a body lumen, and wherein the through hole opens to outside the guide wire insertion portion at both a distal opening portion at a distal end of the guide wire insertion portion and a proximal opening portion at a proximal end of the guide wire insertion portion; and a reinforcing wire element comprising: a coil portion in which a portion of the wire element is wound in a coil so that the coil portion possesses a plurality of axially adjacent windings; and a non-coiled extension portion in which a non-coiled portion of the wire element extends distally away from the coil portion. The proximal-most end of the extension portion is connected to the distal-most end of the coil portion, and the extension portion extends in the axial direction away from the coil portion. The proximal-most end of the coil portion is located proximally of the proximal opening portion of the guide wire insertion portion, and the distal-most end of the extension portion is located distally of the proximal opening portion of the guide wire insertion portion. The coil portion is located between the inner surface of the catheter main body and the outer surface of the catheter main body such that the coil portion is embedded in material forming the catheter main body, with inner and outer surfaces of the coil portion covered.

In accordance with another aspect, the catheter disclosed here includes: an elongated catheter main body having a lumen extending along a longitudinal extent of the catheter main body; a guide wire insertion portion at a distal side of the catheter main body, wherein the guide wire insertion portion is tubular-shaped to receive a guide wire and wherein the guide wire insertion portion includes a distal opening portion and a proximal opening portion; and a reinforcement portion comprised of a coil portion and an extension portion. At least a part of the coil portion is arranged on a proximal side of the proximal opening portion, and the coil portion comprises a wound wire element, and the extension portion is an extension of the wire element of the coil portion that extends to a distal side of the proximal opening portion. The reinforcement portion is positioned between the inner surface of the lumen of the catheter main body and the outer surface of the catheter main body.

The reinforcement portion provided with the coil portion and the extension portion is positioned between the inner surface of the lumen and the outer surface catheter main body so that the reinforcement portion is not exposed inside the lumen. Consequently, it is possible, while improving the anti-kinking property in the vicinity of the proximal opening portion by the reinforcement portion, to prevent an object moving inside the lumen from interfering with the reinforcement portion.

The extension distal portion on the distal end of the extension portion is formed by a curved portion which is formed by bending the wire element, The extension distal portion thus does not exert damage to the material constituting the catheter and is not exposed inside the lumen or inside the body lumen, so that the safety is quite good.

The distal portion of the extension portion can be configured as a bent portion formed by bending a single length of a wire element, and the coil portion is formed by winding the opposite side of the wire element in a coil shape. A catheter having relatively high safety can thus be manufactured rather easily and the work performance when manufacturing is excellent.

The extension portion can be configured so that the bending rigidity decreases from the proximal end toward the distal end in a gradual fashion or in a stepwise fashion. A lower rigidity and higher flexibility toward the distal side can thus be realized in which it is possible to change the bending rigidity of the catheter smoothly and it is also possible to improve the anti-kinking property.

The element wire constituting the extension portion can be configured such that its outer diameter is thinned or reduced toward the distal side, and so it is possible to relatively easily realize a construction having lower rigidity and higher flexibility toward the distal side.

The extension portion can be positioned between the central axis of the guide wire insertion portion and the central axis of the catheter main body. The extension portion can thus be arranged to contact both the guide wire insertion portion and the catheter main body, and it is possible for the bending rigidity between the guide wire insertion portion and the catheter main body to be reinforced efficiently. In addition, it is possible for the extension portion to be arranged approximately parallel with both the central axis of the guide wire insertion portion and the central axis of the catheter main body, so that it is possible to suppress or reduce deviation of the bending rigidity which is caused by inclination with respect to the central axis.

The reinforcement portion can be composed of a metal material to produce sufficient reinforcement strength.

DETAILED DESCRIPTION

Figure 1:
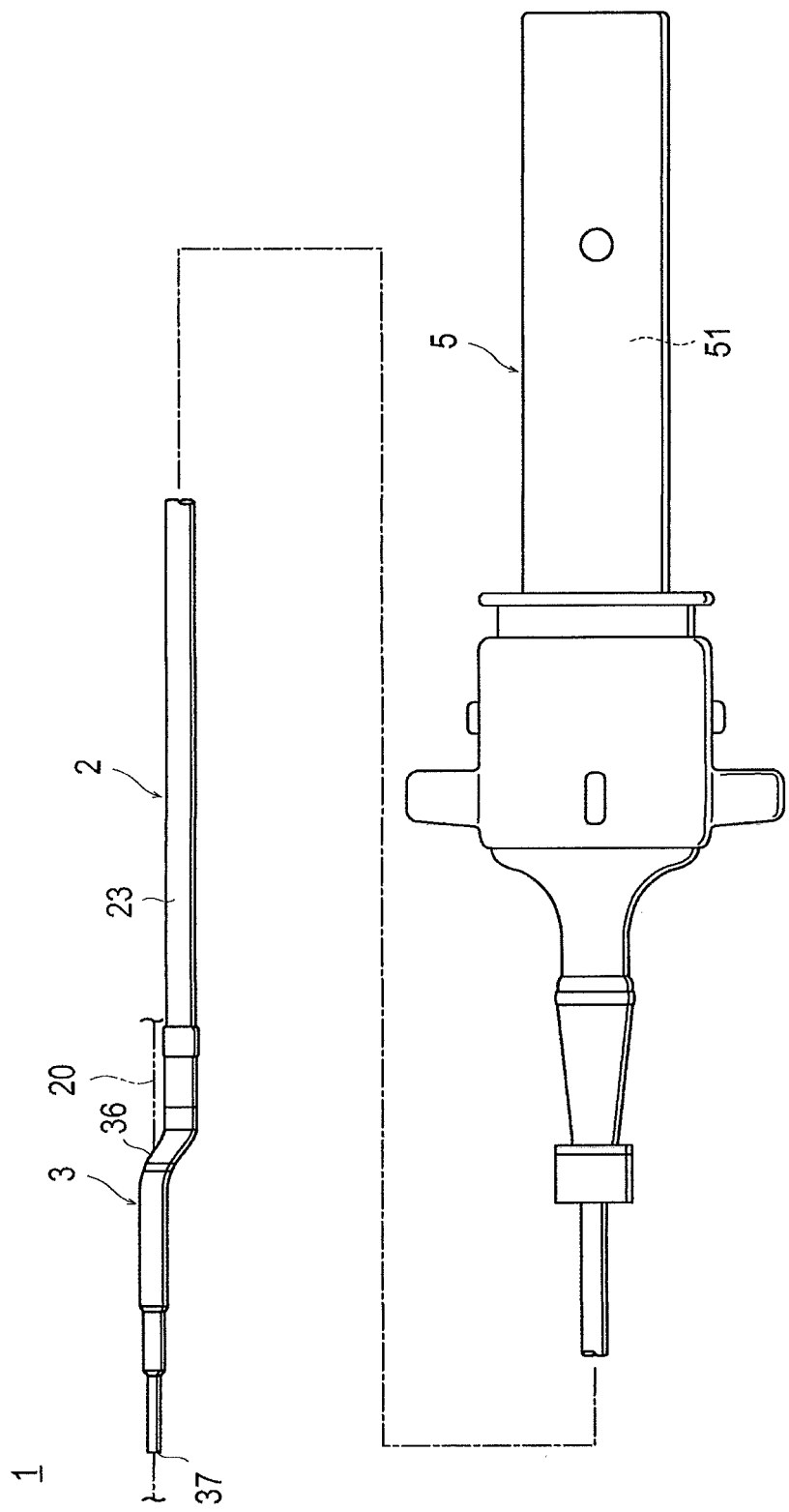
FIG. 1 is a plan view of a catheter according to one embodiment disclosed here by way of example.

Set forth below is a detailed description of several embodiments of a catheter, representing examples of the catheter disclosed here. The following description refers to the accompanying drawing figures which illustrate the catheter and features of the catheter. The drawings may illustrate certain features in an exaggerated manner for convenience in explanation and to facilitate an understanding. The size ratio in the drawings may thus be different from the actual ratio.

A catheter 1 according to a first embodiment is shown in FIG. 1 and includes a catheter main body 2 having an elongated shape and exhibiting flexibility. The catheter is configured (e.g., sized) to be inserted inside a living body such as a body lumen and the like. The catheter 1 also includes a guide wire insertion portion 3 installed on the distal side of the catheter main body 2 and through which a guide wire 20 is insertable, and a connector 5 which is installed on the proximal side of the catheter main body 2 and arranged on the operator's hand side (i.e., is not intended to be inserted inside the living body during use of the catheter) in order to be steered by the operator. The catheter 1 is a so-called "rapid-exchange type" catheter 1 by which it is possible to carry out the pulling-in and pulling-out of the guide wire 20 rapidly. The end of the catheter 1 inserted inside the living body is referred to as the distal end or distal side, and the end not inserted inside the living body is referred to as the proximal end or proximal side.

The guide wire 20 is inserted beforehand to the vicinity of the target lesion inside the living body. The guide wire 20 is inserted before the catheter 1 is inserted inside the living body and is used to introduce the catheter 1 to the target lesion. The catheter 1 is introduced to the target lesion while passing the guide wire 20 through a guide wire lumen 32 positioned at the guide wire insertion portion 3.

Figure 2:
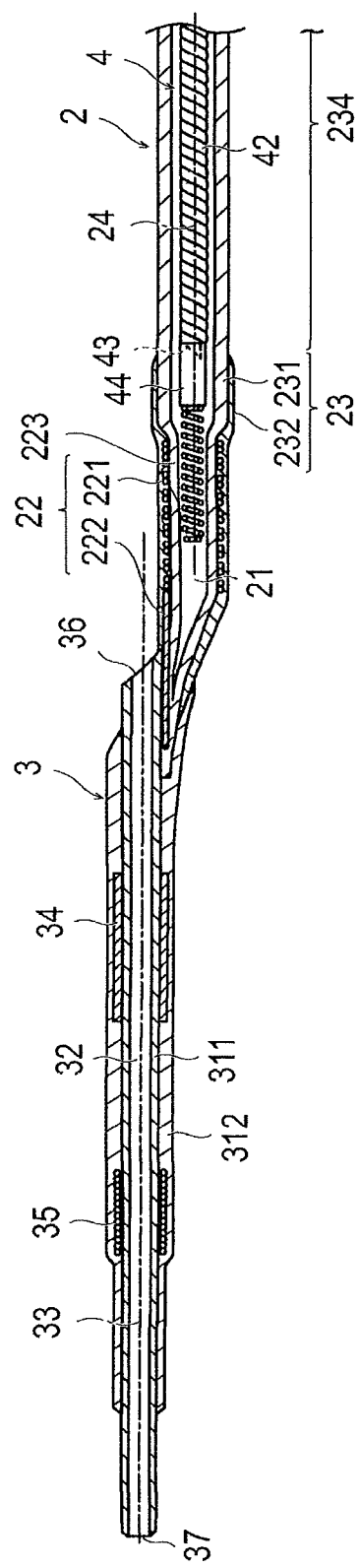
FIG. 2 is a longitudinal cross-sectional view of a distal portion of the catheter shown in FIG. 1.
Figure 3:
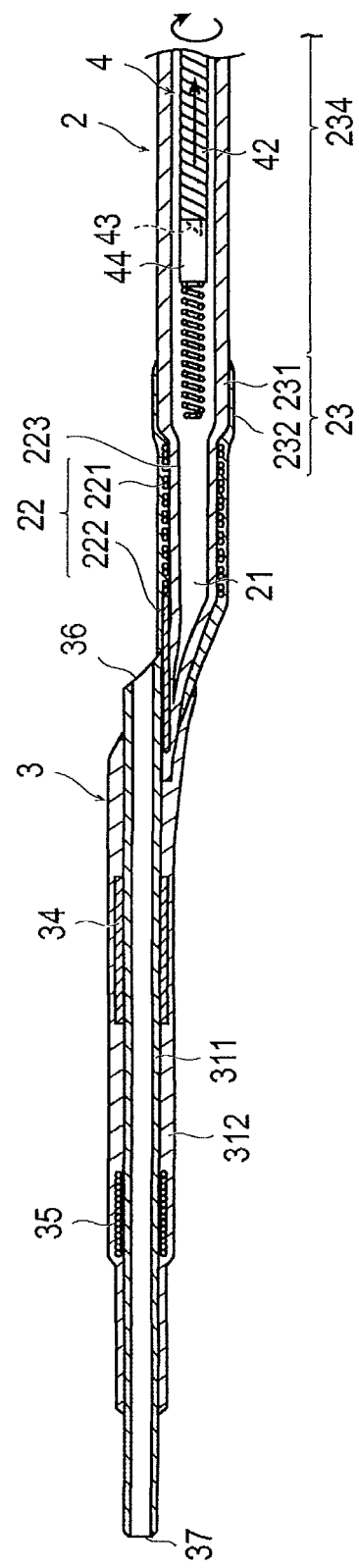
FIG. 3 is a longitudinal cross-sectional view of a distal portion of the catheter shown in FIG. 1.

The catheter main body 2 is provided, as shown in FIG. 2 and FIG. 3, with an axially extending working lumen 21 (lumen) which extends along the longitudinal extent of the main body. This working lumen 21 is a hollow passage in which an image obtaining unit 4 is positioned and is axially movable.

A tube wall 23 which surrounds and defines the working lumen 21 of the catheter main body 2 is constituted by a first layer 231 inside which the working lumen 21 is formed and a second layer 232 covering the outer circumferential surface of the first layer 231 on the distal side of the first layer 231. The material forming the first layer 231 is not limited to a specific material. Examples of materials for the first layer 231 include: fluorine-based resin such as PFA (tetrafluoroethylene-perfluoroalkylvinylether copolymer), FEP (tetrafluoroethylene-hexafluoropropylene copolymer), ETFE (tetrafluoroethylene-ethylene copolymer) and PTFE (polytetrafluoroethylene); pollyamide; polyimide; polyolefin such as polyethylene and polypropylene; polyester such as polyethylene terephthalate and polybutylene terephthalate; polyurethane polystyrene; polycarbonate; silicon resin; and polyetherimide, and within those above, it is preferable to employ a material such as high density polyethylene which has low friction property and also which has high signal permeability. Thus, the friction resistance of the inner surface of the working lumen 21 is reduced and it is possible to move the drive shaft 42 relatively smoothly inside the working lumen 21. The first layer 231 can be formed by a plurality of layers composed of the materials selected from the above-mentioned materials. The material forming the second layer 232 is not particularly limited, but examples of materials which can be used include: various kinds of thermoplastic elastomers such as polyurethane elastomer, polyester elastomer and polyamide elastomer; pollyamide; polyimide; polyolefin such as polyethylene and polypropylene; polyurethane; silicon resin; polyester such as polyethylene terephthalate and polybutylene terephthalate; or a mixture made by mixing two or more kinds of those above, and within those above, it is preferable to employ materials such as various kinds of thermoplastic elastomers, polyurethane and silicon resin which are rich in flexibility comparatively. Thus, it is possible to prevent damage to a body lumen inside of a living body into which the catheter 1 is inserted is damaged.

The tube wall 23 of the catheter main body 2 is constructed such that on the proximal side from the portion of the first layer 231 which is covered by the second layer 232, a window portion 234 is provided. The window portion 234 is constructed to allow the passage of a signal such as a light, ultra-sound and the like. The catheter 1 according to this embodiment disclosed by way of example is a catheter 1 which obtains an image by an optical signal utilizing an optical coherence tomographic image diagnosis technology (Optical Coherent Tomography: OCT) and it is possible to obtain a tomographic image by transmitting and receiving light through the window portion 234.

With respect to the second layer 232, the distal side portion of the second layer 232 extends to a region on the proximal side of the guide wire insertion portion 3 and it covers the circumference of the proximal opening portion 36 of the guide wire lumen 32. Thus, the vicinity of the proximal opening portion 36 of the guide wire insertion portion 3 is reinforced and the occurrence of kinking can be reduced.

The guide wire insertion portion 3 is provided with an inner layer 311 and an outer layer 312 which form tubular shapes. The guide wire insertion portion 3 includes a distal opening portion 37 as illustrated in FIG. 2 at which the guide wire lumen 32 opens on the distal side and the aforementioned proximal opening portion 36 which opens on the proximal side. With respect to the proximal portion of the guide wire insertion portion 3, a portion is interlinked overlappingly with the distal portion of the catheter main body 2. Thus, while maintaining high interlinking strength, there is avoided a large-diameter tendency of the distal portion of the catheter 1. The guide wire insertion portion 3 and the catheter main body 2 are fixed by thermal bonding in this embodiment, but the fixing method is not limited in this regard.

The central axis 33 of the guide wire insertion portion is arranged eccentrically with respect to the center axis 24 of the catheter main body 2. Thus, in the vicinity of the fixing region of the guide wire insertion portion 3 with respect to the catheter main body 2, the guide wire lumen 32 can be secured rather broadly and also in an upright state, so that it is possible to pass through the guide wire 20 more smoothly.

Figure 4:
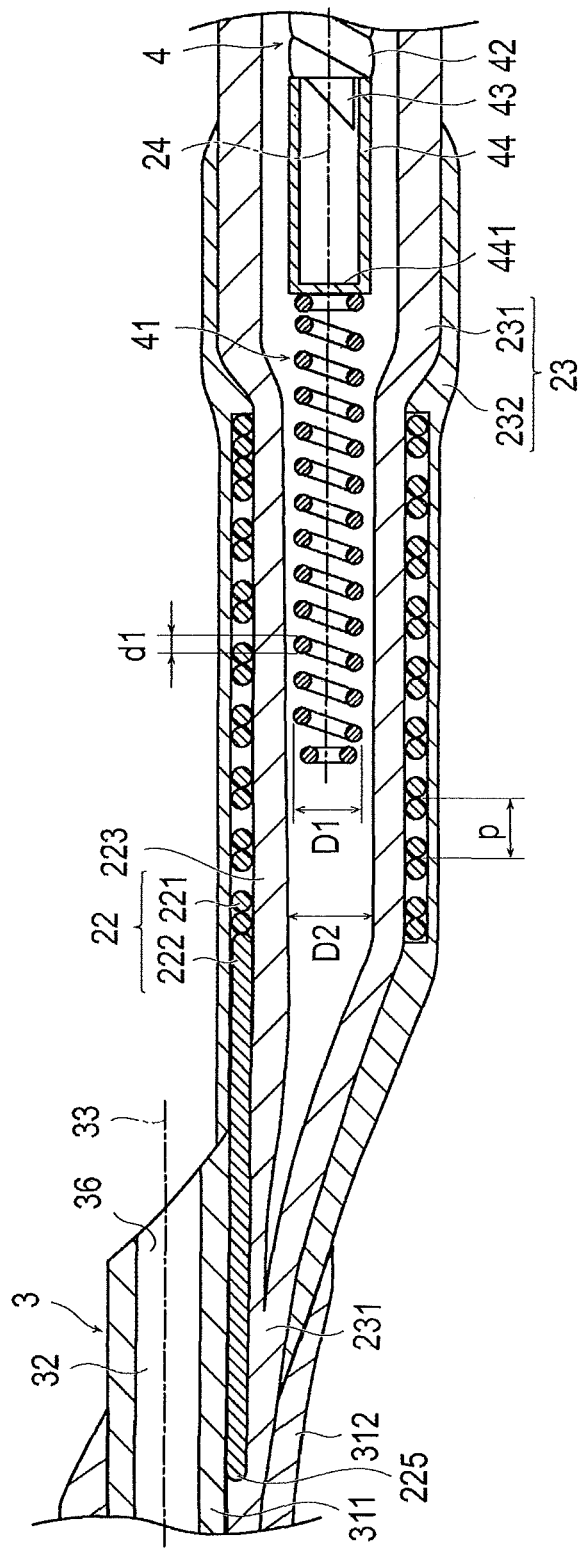
FIG. 4 is an enlarged longitudinal cross-sectional view of a proximal portion of the guide wire insertion portion of the catheter shown in FIG. 1.
Figure 5:
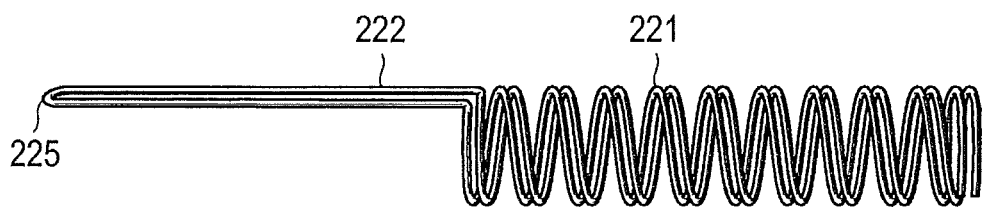
FIG. 5 is a plan view of a reinforcement coil according to one embodiment used in the catheter shown in FIG. 1.

In the vicinity of the boundary of the catheter main body 2 and guide wire insertion portion 3, there is buried and located a reinforcement coil 22 (reinforcement portion) for reinforcing the bending rigidity between the catheter main body 2 and the guide wire insertion portion 3 and for repressing kinking. The reinforcement coil 22 includes, as shown in FIG. 4 and FIG. 5, a coil portion 221 formed by winding a wire element in a spiral shape to produce a plurality of axially adjacent windings, and a non-coiled extension portion 222 axially projecting from one axial end of the coil portion 221 and formed by the wire element wire at the one axial end of the coil being expanded. In the illustrated embodiment, the proximal-most end of the extension portion 222 is connected to the distal-most end of the coil portion 221.

The coil portion 221 is buried and placed concentrically with the working lumen 21 at the distal portion of the working lumen 21 so as to be sandwiched between the first layer 231 and the second layer 232. Thus, in the catheter main body 2, the exposure of the coil portion 221 to the working lumen 21 is blocked and the region in which this exposure is blocked is referred to as an exposure stopper portion 223. The inner diameter and the outer diameter of the exposure stopper portion 223 are diameter-reduced in which the amount of diameter-reduction of the inner diameter is smaller than the amount of diameter-reduction of the outer diameter. A construction thus results in which the wall thickness of the catheter main body 2 on the side of the exposure stopper portion 223 is smaller than that on the proximal side of the tube wall 23. Also, the second layer 232 is coated on or applied to the exposure stopper portion 223. In this manner, while attempting diameter-thinning at the distal portion of the catheter 1, a reasonable rigidity is maintained by providing the coil portion 221 and by coating the second layer 232.

The extension portion 222 extends from the distal side of the coil portion 221 to the distal side away from the proximal opening portion 36 of the guide wire lumen 32, and it is buried and located between the first layer 231 (the outer surface of the first layer 231) of the catheter main body 2 and the inner layer 311 (inner surface of the inner layer 311) of the guide wire insertion portion 3. In this embodiment disclosed by way of example, the surface on the proximal side of the guide wire insertion portion 3 (i.e., the proximal end surface of the guide wire insertion portion 3) is inclined, the proximal opening portion 36 possesses a certain area along the longitudinal or axial direction of the guide wire insertion portion 3, and the extension portion 222 of the reinforcement coil 22 extends on the distal side from the entire area over which the proximal opening portion 36 spreads or extends. That is, the extension portion 222 of the reinforcement coil 22 extends distally beyond the distal-most part of the proximal opening portion 36. It is possible that the extension portion 222 of the reinforcement coil 22 does not extend distally beyond the entire area over which the proximal opening portion 36 spreads. In such a case, the extension portion 222 of the reinforcement coil 22 extends distally beyond the proximal-most part of the proximal opening portion 36.

It is also possible for the extension portion 222 to extend distally beyond the distal end of the first layer 231 of the catheter main body 2 so that the extension portion 222 is buried and located between the inner layer 311 and the outer layer 312 of the guide wire insertion portion 3.

It is preferable for the extension portion 222 to be positioned between the center axis 33 of the guide wire insertion portion 3 and the center axis 24 of the catheter main body 2. Thus, it is possible to arrange the extension portion 222 to contact both the guide wire insertion portion 3 and the catheter main body 2, and it is possible to efficiently reinforce the bending rigidity between the guide wire insertion portion 3 and the catheter main body 2. Also, it is possible to arrange the extension portion 222 approximately parallel with both the center axis 33 of the guide wire insertion portion 3 and the center axis 24 of the catheter main body 2, so that it is possible to reduce deviation in the bending rigidity caused by inclination with respect to the center axis.

With respect to the reinforcement coil 22, a length of a wire element is bent in a U-shape and doubled over, so that an end portion of the bending portion bent in the U-shape is the distal end portion 225 of the extension portion 222, and the coil portion 221 formed by winding the side on which the end portions of the wire element overlap each other. Consequently, the distal portion 225 of the extension portion 222 is formed by a continuous wire of a wire element which is folded back, so that it is formed relatively smoothly. For this reason, for example, even in a case in which the vicinity of the proximal opening portion 36 is deformed significantly, the extension distal portion 225 does not exert damage on the material constituting the catheter 1 and is not exposed inside the guide wire lumen 32, inside the working lumen 21 or inside the body lumen. The catheter 1 thus exhibits excellent safety. Also, even if the extension distal portion 225 is exposed for some reason inside the guide wire lumen 32, inside the working lumen 21 or inside the body lumen, the extension distal portion 225 is formed relatively smoothly, so that the safety thereof can be secured. Also, by simply winding an element wire after being bent, it is easily possible to realize a safe construction, and the work performance during manufacture is excellent.

In this embodiment disclosed by way of example, the coil portion 221 is formed by winding a doubled wire element with a constant pitch p as indicated in FIG. 4, but the pitch p can be changed or varied and, for example, it is also possible to wind the coil by a close coiling such that axially adjacent windings contact each other.

It is possible to employ a construction with respect to the wire element constituting the reinforcement coil 22 such that by using a ring shaped element wire, the wire element is folded back so as to be continuous at both the end portions which became doubled. Also, it is possible to employ a construction which does not involve a doubled-over wire element. It is possible, for example, to employ a single wire, or a tripled-folded wire or a more multiple-folded wire.

The wire element is made of, for example: a stainless steel; a spring steel; a super elastic alloy; a cobalt-based alloy; and a noble metal such as gold, platinum, platinum/iridium alloy and tungsten, or by such as: an alloy containing those metals above, and within them, it is preferable to employ a super elastic alloy, in particular, a Ni—Ti super elastic alloy. If forming the wire element by a metallic material, it is possible to secure the reinforcement strength by the reinforcement coil 22 sufficiently.

As one example, in this embodiment disclosed by way of example, the wire element is produced by a Ni—Ti super elastic alloy having a wire-diameter of 0.05 mm, the inner diameter D1 of the coil portion 221 is 0.64 mm, the outer diameter D2 of the coil portion 221 is 0.74 mm, the pitch P of the coil portion 221 is 0.2 mm, and the length L of the extension portion 222 is 2 mm.

As shown in FIG. 2 and FIG. 3, the guide wire insertion portion 3 includes a reinforcement tube 34 and a marker 35 arranged between the inner layer 311 and the outer layer 312.

The marker 35 is a marker which makes the distal end position of the catheter 1 confirmable or viewable under X-ray fluoroscopy when inserted inside the living body, and it is formed by winding a wire element in a spiral shape and winding the wire element in close coiling such that the neighboring elements or axially adjacent windings contact each other.

It is preferable for the element wire to be a metal material having X-ray impermeability such as: a stainless steel, a super elastic alloy, a cobalt-based alloy, gold, platinum, a platinum/iridium alloy, tungsten and tantalum, and it is produced by a noble metal, an alloy containing those metals or the like. The marker 35 can possess a pipe shape (tubular shape).

The marker 35 is a maker which has contrast imaging properties under X-ray fluoroscopy caused by virtue of the fact that it has an X-ray non-permeability. Such a marker 35 also usually has contrast imaging properties for CT scanning, so that it can be used also in the CT scanning.

The reinforcement tube 34 is a tubular member which is arranged at the proximal portion of the guide wire insertion portion 3.

In a case in which the guide wire 20 which passes through the guide wire lumen 32 and is exposed from the proximal opening portion 36 toward the proximal side is curved and is apart from the catheter main body 2 toward the side thereof during the steering of the catheter 1, there exists a concern that the proximal side of the guide wire insertion portion 3 may be split as a result of the guide wire 20. But the reinforcement tube 34 regulates deformation of the guide wire 20 and fulfills a function of suppressing easily occurring split of the guide wire insertion portion 3.

It is possible for the reinforcement tube 34 to be formed with a spiral-shaped groove extending or wound around the center axis. The groove can be formed on the inner circumferential surface or the outer circumferential surface, or it can be formed on both the inner and outer circumferential surfaces so as to be opened. By providing such a groove, it is possible to keep flexibility of the guide wire insertion portion 3 at which the reinforcement tube 34 is installed and even when inserting the catheter 1 inside a bent lumen of a living body, the following-ability of the guide wire insertion portion with respect to the lumen of the living body is relatively reliably exerted.

Consequently, in the guide wire insertion portion 3, by providing the reinforcement tube 34 having a groove, it is possible to obtain both the conflicting effects of "reinforcement" and "securement of flexibility" at the same time.

There is no limitation to the resin material constituting the reinforcement tube 34. Examples of materials include: PTFE (polytetrafluoroethylene); FEP (tetrafluoroethylene-hexafluoropropylene copolymer); PFA (tetrafluoroethylene-perfluoroalkylvinylether copolymer); ETFE (tetrafluoroethylene-ethylene copolymer); polyolefin such as polyethylene, polypropylene and ethylene-vinyl acetate copolymer; modified polyolefin; pollyamide (example: nylon 6; nylon 46; nylon 66; nylon 610; nylon 612; nylon 11; nylon 12; nylon 6-12; nylon 6-66); thermoplastic polyimide; thermosetting polyimide; liquid crystal polymer such as aromatic polyester; polyphenylene oxide; polyphenylene sulfide; polycarbonate; polymethyl methacrylate; polyether; polyetherketone; polyetherimide; polyacetal; various kinds of thermoplastic elastomers such as stylene-based elastomer, polyolefin-based elastomer, polyvinyl chloride-based elastomer, polyurethane-based elastomer, polyester-based elastomer, pollyamide-based elastomer, polybutadiene-based elastomer, trans-polyisoprene-based elastomer, fluorine rubber-based elastomer and chlorinated polyethylene-based elastomer; or a copolymer, a blended body and a polymer alloy, which make those above to be main materials, and it is possible to use one kind or to use two kinds or more by mixing materials within those above.

The image obtaining unit 4 which is arranged inside the working lumen 21 of the catheter 1 is, as shown in FIGS. 1-3, provided with a transmitting and receiving portion (prism) 43 for transmitting and receiving the light toward the tissue inside the body lumen, a housing 44 for housing the prism 43, a drive shaft 42 having a distal end at which is mounted the housing 44 for transmitting a rotational motive force, a rotation stabilizing coil 41 attached to the distal side of the housing 44, and a scanner 51. The winding direction of the rotation stabilizing coil 41 is the same as the winding direction of the reinforcement coil 22, but it is also possible to employ a winding in the opposite direction.

The prism 43 is a right-angle prism and as shown in FIG. 4, it is fixed at the distal end (distal end of optical fiber) of the drive shaft 42 which is movable forward and backward inside the working lumen 21. The fixing method for fixing the prism 43 to the drive shaft 42 is not limited to a particular method. It is possible to use bonding, and the bonding can be accomplished, for example, by an adhesive agent or by soldering.

The housing 44 is formed in a tubular shape having a distal end closing portion 441 which closes the distal end of the housing 44. The proximal side or end of the housing 44 is fixed on the drive shaft 42. There is no limitation on the specific fixing method. The fixing can be accomplished by bonding, for example by an adhesive agent or by soldering. With respect to the housing 44, an opening portion thereof is formed by cutting off a portion corresponding to the transmitting & receiving portion of the light of the prism 43.

The rotation stabilizing coil 41 is formed by winding a wire element in a spiral shape. The proximal side of the rotation stabilizing coil 41 is fixed at the distal end closing portion 441 of the housing 44 and it serves as a guide for stably rotating the prism 43. The method for fixing the rotation stabilizing coil 41 to the distal end closing portion 441 is not limited. The fixing can be accomplished by bonding, for example bonding by an adhesive agent or by soldering.

It is preferable for the rotation stabilizing coil 41 to be made of a metal material. For example, it can be produced from a metal material having X-ray impermeability such as: a spring steel, a stainless steel, a super elastic alloy, a cobalt-based alloy, gold, platinum and tungsten, or by an alloy containing those metals. It is also possible for the rotation stabilizing coil 41 to be manufactured from a material other than metal material.

The rotation stabilizing coil 41 is housed inside the exposure stopper portion 223 when the drive shaft 42 is pressed or moved in the distal direction to the maximum extent. At that time, the movement of the drive shaft 42 is regulated by a limit switch of an axial direction move stage of the scanner and the pressing or axial movement is stopped, so that it is constructed so that the drive shaft is pressed onto the exposure stopper portion 223 and is not destructed.

When the rotation stabilizing coil 41 is housed in the exposure stopper portion 223, the reinforcement coil 22 and the rotation stabilizing coil 41 axially overlap each other, but the reinforcement coil 22 is covered by the first layer 231 and is not exposed to the inside of the working lumen 21, so that it is possible to reliably prevent biting between the coils of the reinforcement coil 22 and the coils of the rotation stabilizing coil 41.

Also, when the rotation stabilizing coil 41 enters the exposure stopper portion 223, the rotation stabilizing coil 41 overlaps the reinforcement coil 22 at the inside of the reinforcement coil 22, so that at the distal end of the catheter main body 2, the image obtaining unit 4 and the catheter main body 2 exhibit a one-body configuration. When inserting the catheter 1 inside the living body, a structure is realized which has a strong resistance against the bending (anti-kink structure).

The drive shaft 42 is flexible and also has the ability to transmit rotational motion power produced in the connector 5 to the prism 43. By way of example, the drive shaft 42 has a construction involving a tubular body with a multi-layer coil shape and having a constant outer diameter.

A connector 5 is connected on the proximal side of the catheter main body 2. The connector 5 is provided, for example, with an optical fiber connector in the inside thereof, and it is possible to connect the drive shaft 42 having an optical fiber in the inside thereof to a scanner 51 for rotating the drive shaft 42 in a relatively high speed. It is possible for the scanner 51 to communicate the optical signal from the prism 43, which is transmitted through the optical fiber inside the drive shaft 42, to an exclusive analyzing apparatus. In this communication state, it is possible to display, on an image display apparatus, the tomographic image inside the lumen of the living body which is constructed by the analyzing apparatus.

When obtaining an image by the image obtaining unit 4, as shown in FIG. 2 and FIG. 3, the drive shaft 42 is axially moved in the distal direction to the maximum extent, and while moving the drive shaft 42 toward the proximal direction along the working lumen 21 from an insertion state in which the rotation stabilizing coil 41 is inserted into the reinforcement coil 22, the drive shaft 42 is steered so as to rotate around its central axis. In synchronized with the spiral motion of such a drive shaft 42, the prism 43 also moves in a spiral manner and it is possible to obtain a tomographic image over the longitudinal direction inside the body lumen.

When obtaining a tomographic image again, the drive shaft 42 is moved toward the distal side and, by setting a state as shown in FIG. 2, it is possible to implement an image obtaining process again. At that time, there is provided with the exposure stopper portion 223, so that it is possible for the operator to insert the rotation stabilizing coil 41 into the reinforcement coil 22 without any contact and it is possible to prevent a damage and a biting of the reinforcement coil 22 and the rotation stabilizing coil 41. Further, the exposure stopper portion 223 functions also as a push-in stopper for stopping the movement of the drive shaft 42, so that it is possible to arrange the drive shaft 42 at an appropriate position reliably.

Figure 6:
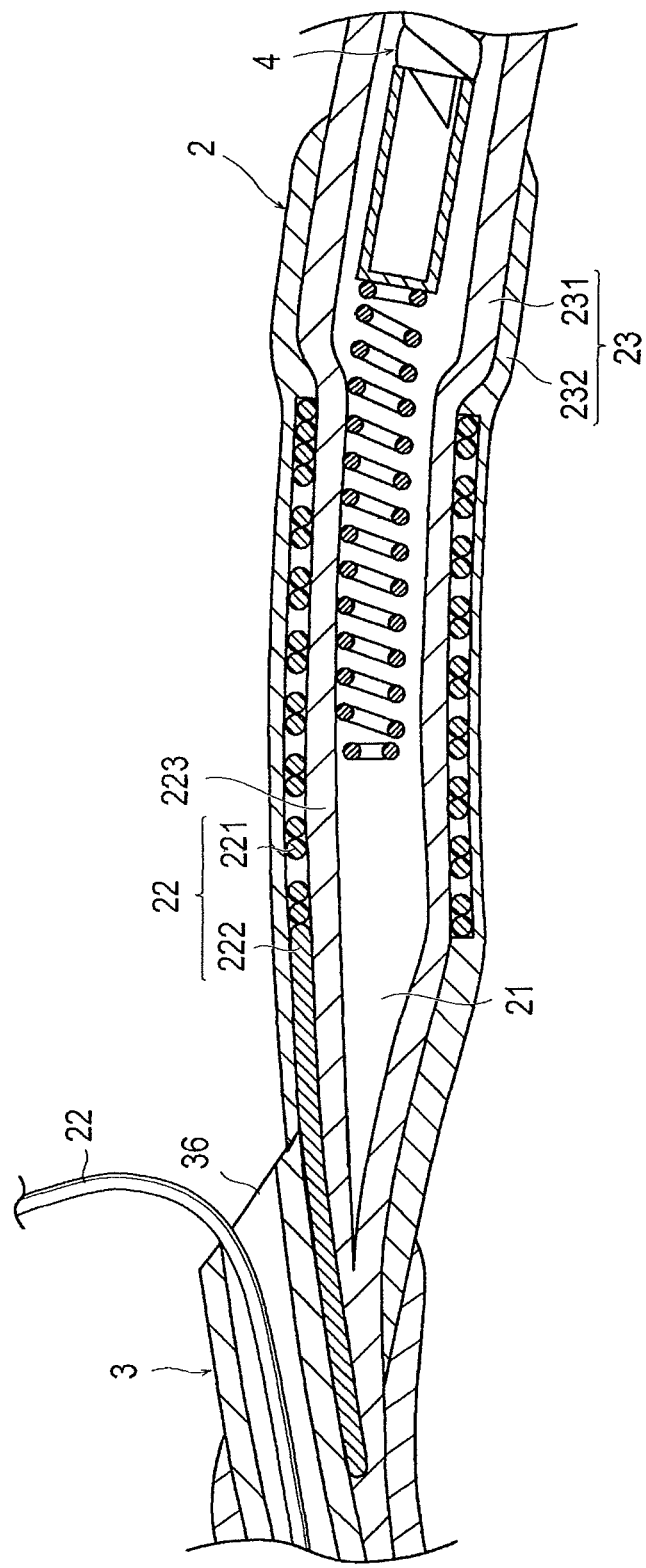
FIG. 6 is a longitudinal cross-sectional view of the proximal side of the guide wire insertion portion when the catheter shown in FIG. 1 is bent.

As mentioned above, it is possible for the catheter 1 to be positioned in an insertion state in which the rotation stabilizing coil 41 is inserted into the reinforcement coil 22. In this insertion state, if a pressing force, for example, acts on the guide wire 20 and this pressing force is transmitted to the guide wire insertion portion 3, as shown in FIG. 6, a bending occurs in a vicinity of the boundary portion between the catheter main body 2 and the guide wire insertion portion 3. Even if such a bending occurs, the exposure stopper portion 223 intervenes between the rotation stabilizing coil 41 and the reinforcement coil 22 to prevent "biting" in which both wire elements interleave with each other, and so there is no interference between the coils of the wire elements. Consequently, if the afore-mentioned pressing force is canceled, as shown in FIG. 2 and FIG. 4, the rotation stabilizing coil 41 and the reinforcement coil 22 can restore the original shapes, and there is realized a catheter 1 which has an excellent anti-kinking property.

Also, in an insertion state shown in FIG. 4 and in a natural state in which a bending does not occur, the outer circumferential portion of the rotation stabilizing coil 41 is spaced from the exposure stopper portion 223. It is preferable for the difference between the maximum outer diameter D1 of the rotation stabilizing coil 41 and the inner diameter D2 of the exposure stopper portion 223 to be identical or less than the wire-diameter d1 of the wire element of the rotation stabilizing coil 41. In a case in which the rotation stabilizing coil 41 is spaced from the exposure stopper portion 223, even if bending occurs at the reinforcement coil 22, it is possible to prevent the exposure stopper portion 223 from contacting the rotation stabilizing coil 41 depending on the degree of bending. Even if the exposure stopper portion 223 supposedly contacts to the rotation stabilizing coil 41, the influence exerted to the rotation of the drive shaft 42 is very small.

The extension portion 222 extending from the coil portion 221 of the reinforcement coil 22 extends on the distal side of the proximal opening portion 36 of the guide wire insertion portion 3. It is thus possible to improve the bending rigidity in the vicinity of the proximal opening portion 36 of the distal side away from the coil portion 221. Thus, there is improved the anti-kinking property in the vicinity of the proximal opening portion 36 in which the rigidity may be discontinuous and a kinking occurs more easily. In particular, the extension portion 222 extends from the wire element of the coil portion 221 and is formed continuously, so that also the bending rigidity becomes continuous and there is obtained excellent anti-kinking properties.

Also, the reinforcement coil 22 is provided within narrow range of the boundary portion between the guide wire insertion portion 3 and the catheter main body 2, and it is possible to heighten the rigidity thereof, so that it is possible to arrange the prism 43 on the distal side as much as possible inside the catheter 1. Consequently, when inserting the catheter 1 inside the body lumen, the tomographic image can be obtained from the distal side of the catheter 1 as much as possible. It is thus possible to widen the measurement range or reduce the burden on a patient by reducing the insertion amount of the catheter 1 inside the body lumen.

Also, it is possible for the reinforcement coil 22 to be buried inside the first layer 231 or the second layer 232.

Figure 7:
FIG. 7 is a plan view of a reinforcement coil used for a catheter according to a second embodiment disclosed by way of example.

FIG. 7 illustrates a catheter according to a second embodiment disclosed by way of example. The following description focuses primarily on differences between this embodiment and the first embodiment. Features in this second embodiment of the catheter that are similar to those in the first embodiment are identified by common reference numerals and a detailed description of such features is not repeated.

The catheter according to the second embodiment includes, as shown in FIG. 7, includes a reinforcement coil 22A provided with a coil portion 221A and an extension portion 222A extending from the coil portion 221A. The wire element constituting the extension portion 222A is formed that it gradually becomes thinner toward the distal portion 225A. In the illustrated embodiment, the wire element constituting the extension portion 222A gradually becomes thinner from the proximal end or side of the extension portion 222A toward the distal end portion 225A. That is, the portion of the wire element forming the extension portion 222A becomes gradually smaller in outer diameter toward the distal end portion 225A. The position at which the reinforcement coil 22A is placed in the catheter is similar to that of the first embodiment. If employing such a construction, the extension portion 222A has lower rigidity and more flexibility toward the distal end and it is possible to change the bending rigidity smoothly from the region which is provided with the reinforcement coil 22A in the catheter toward the guide wire insertion portion 3, and it is possible to improve the anti-kinking property of the catheter.

An example of a method for narrowing the extension portion 222A toward the distal end include a chemical polishing method. In a case in which the reinforcement coil 22A is made of a Ni—Ti super elastic alloy, by using a chemical of Hydrofluoric acid or the like and by adjusting an immersion time with respect to the chemical, it is possible to make the wire-diameter of the wire element finer in an inclined fashion or gradual manner.

Figure 8:
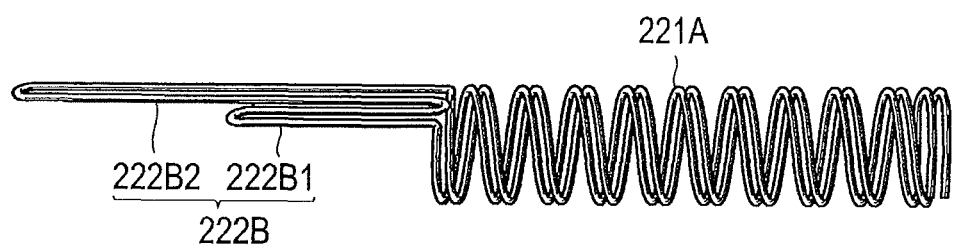
FIG. 8 is a plan view of a reinforcement coil used for a catheter according to a third embodiment disclosed by way of example.

FIG. 8 illustrates a catheter according to a third embodiment disclosed by way of example. The following description focuses primarily on differences between this embodiment and the first embodiment. Features in this third embodiment of the catheter that are similar to those in the above-described embodiments are identified by common reference numerals and a detailed description of such features is not repeated.

The catheter according to the third embodiment includes, as shown in FIG. 8, a reinforcement coil 22B in which a plurality of extension portions 222B (222B1, 222B2) are formed by folding back the wire element extending from the coil portion 221B a plurality of times. By appropriately selecting the lengths of the extension portions 222B1, 222B2 to be different from one another, it is possible to change the bending rigidity in a stepwise fashion. More specifically, in this embodiment, by providing the relatively shorter extension portion 222B1 and the relatively longer extension portion 222B2, the number of wire elements contributing to the bending rigidity is reduced from four pieces to two pieces from the proximal side toward the distal side. In this way, the bending rigidity of the distal end in the extension portion 222B is smaller than that of the proximal end. The position at which the reinforcement coil 22B is placed in the catheter is similar to that of the first embodiment. If employing such a construction, it is possible to reduce the bending rigidity of the reinforcement coil 22B in a stepwise fashion from the proximal end toward the distal end, so that it is possible to change the bending rigidity in the catheter relatively smoothly and it is possible to improve the anti-kinking property of the catheter. The number of extension portions 222B is not limited two, as it is possible to employ three or more pieces. Also, with respect to the respective lengths of the plurality of extension portions 222B1, 222B2, it is possible to use not extension portions having different lengths, but also extension portions that are equal in length.

Figure 9:
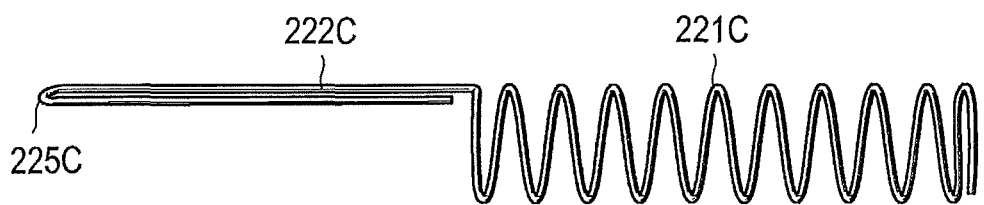
FIG. 9 is a plan view of a reinforcement coil used for a catheter according to a fourth embodiment disclosed by way of example.

FIG. 9 illustrates a catheter according to a fourth embodiment disclosed by way of example. The following description focuses primarily on differences between this embodiment and the first embodiment described above. Features associated with this fourth embodiment of the catheter that are similar to those in the embodiments described above are identified by common reference numerals and a detailed description of such features is not repeated.

The catheter according to the fourth embodiment includes, as shown in FIG. 9, a reinforcement coil 22C in which a coil portion 221C is constructed of a single-phase wire coil and an extension portion 222C is constructed by folding back the wire element extending from the coil portion 221C at an extension distal portion 225C. It should be noted that the position at which the reinforcement coil 22C is placed in the catheter is similar to that of the first exemplified embodiment. By virtue of this construction, as in the first embodiment, it is possible to form the extension distal portion 225C of the reinforcement coil 22C in a smooth shape and it is possible to secure the safety.

Hereinafter, with reference to FIG. 10, there will be explained a catheter 1D according to a fifth embodiment. The description which follows focuses primarily on differences between this embodiment and the first embodiment. Features in this fifth embodiment of the catheter that are similar to those in the embodiments described above are identified by common reference numerals and a detailed description of such features is not repeated.

Figure 10:
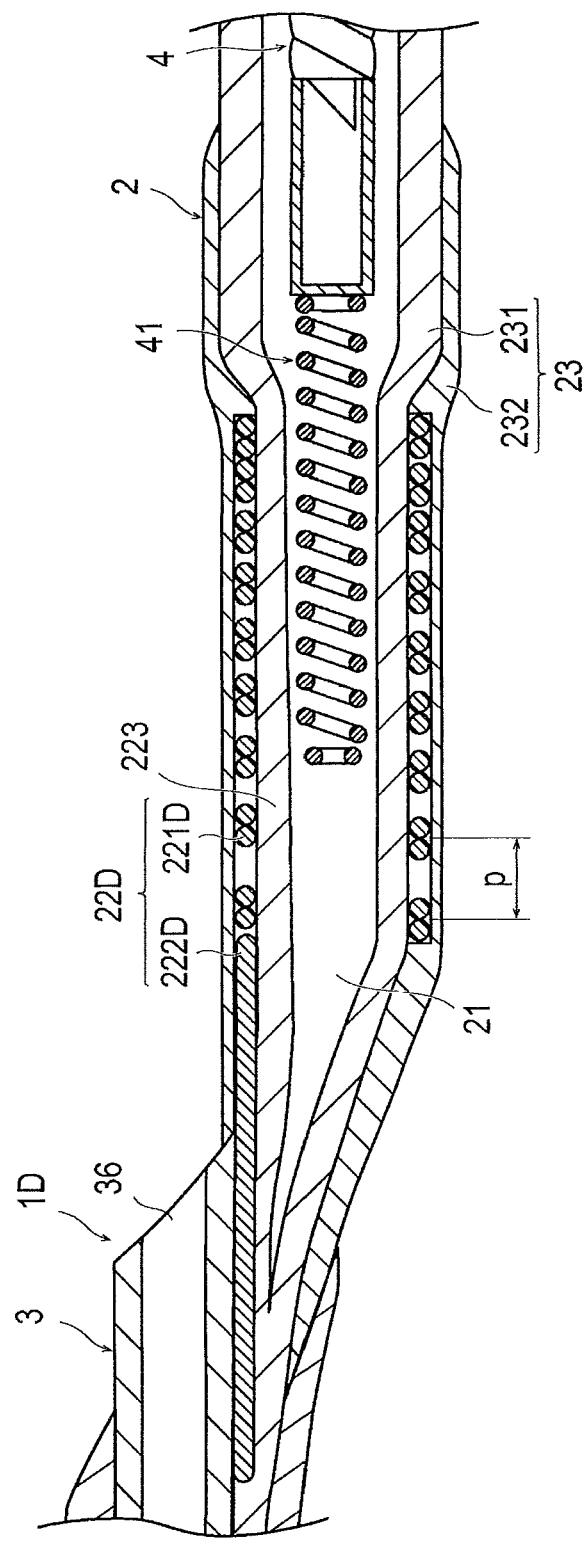
FIG. 10 is a longitudinal cross-sectional view of a proximal side of a guide wire insertion portion of a catheter according to another embodiment disclosed by way of example.

The catheter 1D according to the fifth embodiment, as shown in FIG. 10, is configured so that the pitch p between axially adjacent wire elements of a coil portion 221D of the reinforcement coil 22D which includes the coil portion 221D and the extension portion 222D is different along the longitudinal or axial direction. The pitch p is set to be narrower toward the proximal side and broader toward the distal side. With this construction, the bending rigidity of the reinforcement coil 22D decreases in an inclined or gradual fashion from the proximal end toward the distal end, so that it is possible to change the bending rigidity for the catheter 1D relatively smoothly and it is possible to improve anti-kinking property in the vicinity of the proximal opening portion 36 of the catheter 1D.

Figure 11:
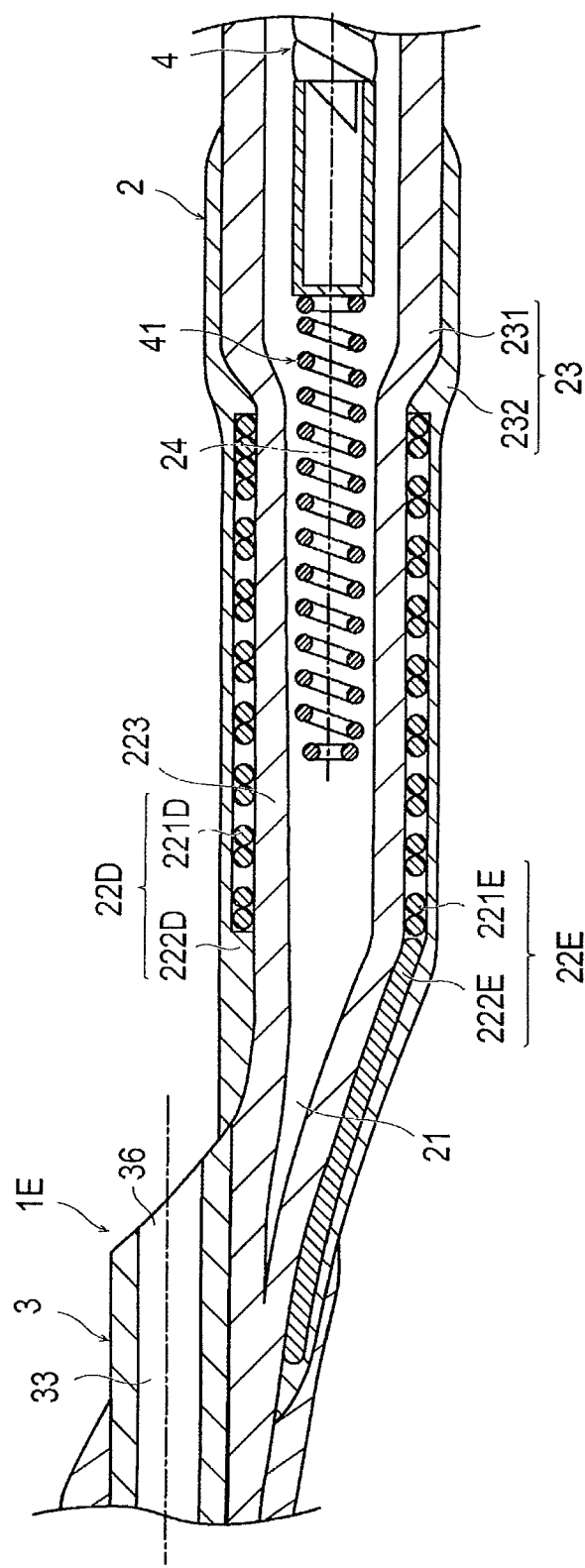
FIG. 11 is a longitudinal cross-sectional view of a proximal side of a guide wire insertion portion of a catheter according to a further embodiment disclosed by way of example.

Referring to FIG. 11, there will be explained a catheter 1E according to a sixth exemplified embodiment. The following description focuses primarily on differences between this embodiment and the first embodiment. Features in this sixth embodiment of the catheter that are similar to those in the embodiments described above are identified by common reference numerals and a detailed description of such features is not repeated.

The catheter 1E according to the sixth embodiment, as shown in FIG. 11, includes an extension portion 222E extending from a coil portion 221E of the reinforcement coil 22E, but the extension portion 222E is not positioned between the center axis 33 of the guide wire insertion portion 3 and the center axis 24 of the catheter main body 2. Rather, the extension portion 222E is positioned on the opposite side of the center axis 33 of the guide wire insertion portion 3 with respect to the center axis 24 of the catheter main body. In this manner, it is possible to set the circumferential directional position at which the extension portion 222E of the reinforcement coil 22E is arranged to be at a different position from that of the first embodiment in which it is provided between the center axis 33 and the center axis 24. Employing such a construction, it is possible to change the bending rigidity in the vicinity of the proximal opening portion 36 of the catheter 1E relatively smoothly and it is possible to improve anti-kinking property of the catheter 1E. The circumferential direction position at which the extension portion 222E extends or is expanded is not limited to the position shown in FIG. 11 as the position can be changed appropriately.

The catheter disclosed here is not limited to the various embodiments disclosed by way of example, and it is possible to make alterations. For example, in the embodiments discussed above and illustrated in the drawing figures, the disclosure is discussed in the context of a catheter for diagnosis utilizing an optical coherence tomographic image technology (OCT). But it is also possible to apply the disclosure here to other catheters for diagnosis. For example, it is possible to use the disclosure here in an ultra-sound catheter utilizing an ultrasonic transducer. In the ultra-sound catheter, it is possible to observe a living body by introducing an ultra-sound into the living body and based on the ultra-sound returning after being scattered or being absorbed, or after being reflected or being refracted inside the living body. Consequently, it is possible for the detection wave to apply not only the light but also all kinds of waves which are applicable for the detection of such as ultra-sound, magnetic field, sound and the like. In addition, it is also possible to apply a plurality of features of the exemplified embodiments mentioned above in combination.

The detailed description above describes a catheter according to several embodiments disclosed by way of example. The invention here is not limited, however, to the precise embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A catheter comprising:
   an elongated catheter main body having an axially extending lumen that is closed at a distal end of the lumen, the catheter main body comprising a first layer inside which the lumen extends and a second layer positioned radially outside the first layer and covering an outer circumferential surface of a part of an axial extent of the first layer, the first and second layers being made of different material compositions, the second layer possessing a proximal-most end positioned distal of a proximal-most end of the first layer, the first layer possessing an inner surface surrounding the lumen, the catheter main body also possessing a distal end portion;
   a guide wire insertion portion at the distal end portion of the catheter main body, with a through hole passing through the guide wire insertion portion and configured to receive a guide wire allowing the catheter to be guided to a target site in a body lumen, the through hole opening to outside the guide wire insertion portion at both a distal opening portion at a distal end of the guide wire insertion portion and a proximal opening portion at a proximal end of the guide wire insertion portion;
   a reinforcing wire element comprising: a coil portion in which a portion of the wire element is wound in a coil so that the coil portion possesses a plurality of axially adjacent windings; and a non-coiled extension portion in which a non-coiled portion of the wire element extends distally away from the coil portion;
   the coil portion and the non-coiled portion each possessing an inner surface and an outer surface, the reinforcing wire element being positioned between the first and second layers such that the inner surface of the coil portion is in contact with the first layer and the outer surface of the coil portion is in contact with the second layer, and such that the inner surface of the non-coiled portion is in contact with the first layer and the outer surface of the non-coiled portion is in contact with the second layer;
   the non-coiled extension portion of the reinforcing wire element and the coil portion of the reinforcing wire element being integrally formed so that the non-coiled extension portion and the coil portion are unitary with each other, the non-coiled extension portion of the reinforcing wire element being bent in a U-shape and doubled over;
   the coil portion possessing a proximal-most end and a distal-most end, the extension portion possessing a proximal-most end and a distal-most end, the proximal-most end of the extension portion being connected to the distal-most end of the coil portion, and the extension portion extending in an axial direction away from the coil portion;
   the proximal-most end of the coil portion being located proximally of the proximal opening portion of the guide wire insertion portion;
   the distal-most end of the extension portion being located distally of the proximal opening portion of the guide wire insertion portion; and
   the coil portion being located between the inner surface of the catheter main body and the outer surface of the catheter main body such that the coil portion is embedded in material forming the catheter main body, with inner and outer surfaces of the coil portion covered.

2. The catheter according to claim 1, wherein the non-coiled extension portion is a first non-coiled extension portion, and including a second non-coiled extension portion positioned side-by-side relative to the first non-coiled extension portion, the second non-coiled extension portion being bent in a U-shape and doubled over.

3. The catheter according to claim 2, wherein an axial length of the second non-coiled extension portion, measured from a distal end of the coil portion to a distal end of the second non-coiled extension portion, is shorter than an axial length of the first non-coiled extension portion, measured from the distal end of the coil portion to a distal end of the first non-coiled extension portion.

4. The catheter according to claim 1, wherein the extension portion is configured so that a bending rigidity of the extension portion decreases from a proximal end of the extension portion toward the distal-most end of the extension portion in a step-wise manner.

5. The catheter according to claim 4, wherein the wire element possesses an outer diameter, and wherein the outer diameter of the wire element in the extension portion is reduced toward the distal-most end of the extension portion.

6. The catheter according to claim 1, wherein the extension portion is configured so that a bending rigidity of the extension portion decreases from a proximal end of the extension portion toward the distal-most end of the extension portion in a gradual manner.

7. The catheter according to claim 6, wherein the wire element possesses an outer diameter, and wherein the outer diameter of the wire element in the extension portion is reduced toward the distal-most end of the extension portion.

8. The catheter according to claim 1, wherein the catheter main body and the guide wire insertion portion each possess a central axis, wherein the central axis of the catheter main body and the central axis of the guide wire insertion portion are non-coaxially arranged, and wherein the extension portion is positioned between the central axis of the guide wire insertion portion and the central axis of the catheter main body.

9. The catheter according to claim 1, wherein the coil portion and the extension portion are made of a metal material.

10. The catheter according to claim 1, wherein the coil portion possesses an axial extent from one end of the coil portion to an opposite end of the coil portion, the non-coiled portion possessing an axial extent from one end of the non-coiled portion to an opposite end of the non-coiled portion, the inner surface of the coil portion over the entire axial extent of the coil portion being in contact with the first layer, the outer surface of the coil portion over the entire axial extent of the coil portion being in contact with the second layer, the inner surface of the non-coiled portion being in contact with the first layer over the entire axial extent of the non-coiled portion, and the outer surface of the non-coiled portion being in contact with the second layer over only a part of the axial extent of the non-coiled portion.

11. A catheter according to claim 1, wherein the lumen in the catheter main body possesses a smoothly-shaped surface.

12. The catheter according to claim 1, wherein the lumen of the main body possesses a center axis and the through hole of the guide wire insertion portion possesses a central axis, and wherein the coil portion of the reinforcing wire element is concentric with the lumen of the main body, and the central axis of the guide wire insertion portion is eccentric with respect to the center axis of the main body.

13. The catheter according to claim 1, wherein the proximal portion of the guide wire insertion portion and the distal portion of the catheter main body are fixed together and axially overlap each other.

14. The catheter according to claim 1, wherein the lumen in the catheter main body is configured so that an image obtaining unit is positionable in the lumen of the catheter main body and is movable within the lumen.

15. The catheter according to claim 1, wherein
the distal end portion of the catheter main body includes a stopper section possessing a smaller inner diameter than the distal end portion of the catheter main body positioned immediately proximal of the stopper section, and
the proximal-most end of the coil portion is located in the stopper section possessing the smaller inner diameter.

16. A catheter comprising:
an elongated catheter main body having a lumen extending along a longitudinal extent of the catheter main body, the lumen possessing a distal end that is closed;
a guide wire insertion portion at a distal side of the catheter main body, the guide wire insertion portion being tubular-shaped to receive a guide wire, the guide wire insertion portion including a distal opening portion and a proximal opening portion;
a reinforcement portion comprised of a coil portion and an extension portion, at least a part of the coil portion being arranged on a proximal side of the proximal opening portion, the coil portion comprising a wound wire element, the extension portion being an integral extension of the wire element of the coil portion that extends to a distal side of the proximal opening portion so that the extension portion and the coil portion are unitary with each other;
the extension portion being an axially extending U-shaped portion of the wire element that is doubled over; and
the reinforcement portion being positioned between an inner surface of the lumen of the catheter main body and an outer surface of the catheter main body.

17. The catheter according to claim 16, wherein the extension portion is an axially extending first extension portion, and including an axially extending second extension portion positioned side-by-side relative to the axially extending first extension portion.

18. The catheter according to claim 17, wherein an axial length of the axially extending second extension portion, measured from a distal end of the coil portion to a distal end of the second non-coiled extension portion, is axially shorter than an axial length of the axially extending first extension portion, measured from the distal end of the coil portion to a distal end of the first non-coiled extension portion.

19. The catheter according to claim 16, wherein the extension portion is configured so that a bending rigidity of the extension portion decreases from a proximal end of the extension portion toward the distal-most end of the extension portion in a step-wise or gradual manner.

20. The catheter according to claim 19, wherein the wire element possesses an outer diameter, and wherein the outer diameter of the wire element in the extension portion is reduced toward the distal-most end of the extension portion.

21. The catheter according to claim 16, wherein the catheter main body and the guide wire insertion portion each possess a central axis, wherein the central axis of the catheter main body and the central axis of the guide wire insertion portion are non-coaxially arranged, and wherein the extension portion is positioned between the central axis of the guide wire insertion portion and the central axis of the catheter main body.

22. The catheter according to claim 16, wherein the coil portion and the extension portion are made of a metal material.

23. The catheter according to claim 16, wherein the lumen in the catheter main body is closed at a distal end of the lumen coil portion and the non-coiled portion are positioned between first and second layers of materials having different material compositions.

24. The catheter according to claim 16, wherein the lumen of the main body possesses a center axis and the tubular-shaped guide wire insertion portion possesses a central axis, and wherein the coil portion of the reinforcement portion is concentric with the lumen of the main body, and the central axis of the tubular-shaped guide wire insertion portion is eccentric with respect to the center axis of the lumen of the main body.

25. The catheter according to claim 16, wherein the coil portion of the reinforcement portion includes a plurality of axially adjacent helical windings with respective spaces between at least some of the axially adjacent helical windings so that the at least some of the axially adjacent helical winding are spaced from one another so as not to be in contact with one another, wherein the main body is formed of a material, and the material forming the catheter main body spans the spaces between at least some of the axially adjacent helical windings.

26. A catheter comprising:
- an elongated catheter main body having a lumen extending along a longitudinal extent of the catheter main body, the lumen in the catheter main body possessing a central axis;
- a guide wire insertion portion at a distal side of the catheter main body, the guide wire insertion portion possessing a guide wire lumen to receive a guide wire, the guide wire lumen being open at a distal opening portion of the guide wire insertion portion and being open at a proximal opening portion of the guide wire insertion portion, the guide wire lumen possessing a central axis; the central axis of the guide wire lumen being spaced radially outwardly of the central axis of the lumen in the catheter main body;
- a reinforcement portion comprised of a coil portion and an extension portion, at least a part of the coil portion being arranged on a proximal side of the proximal opening portion, the coil portion comprising a wound wire element, the extension portion being an axially extending integral extension of the wire element so that the extension portion and the coil portion are unitary with each other, at least a part of the axially extending extension axially overlapping the guide wire lumen;
- the extension portion being an axially extending U-shaped portion of the wire element that is doubled over and extends distally beyond a distal-most end of the coil portion; and
- the reinforcement portion being positioned between an inner surface of the lumen of the catheter main body and an outer surface of the catheter main body.

\* \* \* \* \*